US011959887B2

(12) United States Patent
Jaaskelainen et al.

(10) Patent No.: US 11,959,887 B2
(45) Date of Patent: Apr. 16, 2024

(54) ASYMMETRIC FLUIDIC OSCILLATOR FOR GENERATING A WELLBORE SIGNAL

(71) Applicant: Halliburton Energy Services, Inc., Houston, TX (US)

(72) Inventors: Mikko K. Jaaskelainen, Katy, TX (US); Julian Drew, Centennial, CO (US); Benjamin Schaeffer, Denver, CO (US)

(73) Assignee: Halliburton Energy Services, Inc., Houston, TX (US)

( * ) Notice: Subject to any disclaimer, the term of this patent is extended or adjusted under 35 U.S.C. 154(b) by 46 days.

(21) Appl. No.: 17/832,126

(22) Filed: Jun. 3, 2022

(65) Prior Publication Data

US 2023/0393102 A1 Dec. 7, 2023

(51) Int. Cl.
*G01N 29/34* (2006.01)
*G01N 29/02* (2006.01)
*G01N 33/28* (2006.01)
*E21B 47/14* (2006.01)

(52) U.S. Cl.
CPC .......... *G01N 29/348* (2013.01); *G01N 29/02* (2013.01); *G01N 33/2823* (2013.01); *E21B 47/14* (2013.01); *G01N 2291/02809* (2013.01); *G01N 2291/02818* (2013.01); *G01N 2291/02836* (2013.01)

(58) Field of Classification Search
CPC .. G01N 29/348; G01N 29/02; G01N 33/2823; G01N 2291/02809; G01N 2291/02818; G01N 2291/02836; E21B 47/14
See application file for complete search history.

(56) References Cited

U.S. PATENT DOCUMENTS

| 2005/0214147 | A1 | 9/2005 | Schultz et al. | |
|---|---|---|---|---|
| 2007/0261486 | A1* | 11/2007 | Fallet | E21B 47/10 73/152.29 |
| 2012/0292116 | A1* | 11/2012 | Schultz | E21B 28/00 137/809 |
| 2013/0042699 | A1 | 2/2013 | Schultz et al. | |
| 2021/0114044 | A1* | 4/2021 | Zhao | B05B 1/04 |

OTHER PUBLICATIONS

Halliburton Energy Services, Inc., International Search Report and Written Opinion, PCT/US2022/032190, dated Feb. 27, 2023, 11 pages.
Halliburton Energy Services, Inc , "Oil and Gas Well Multi-Phase Fluid Flow Monitoring With Multiple Transducers and Machine Learning", Unpublished U.S. Appl. No. 63/263,89, filed Feb. 18, 2022.

* cited by examiner

*Primary Examiner* — Tarun Sinha
(74) *Attorney, Agent, or Firm* — Kilpatrick Townsend & Stockton LLP (57) ABSTRACT

An asymmetric fluidic oscillator can generate acoustic signals in a wellbore. The asymmetric fluidic oscillator can include an inlet housing defining an inlet channel, a feedback system, and an outlet housing defining an outlet channel. The inlet channel can be sized to receive fluid from the wellbore. The feedback system can be coupled to the inlet channel to oscillate the fluid from the wellbore. The outlet channel can be coupled to the feedback system and can be sized to receive the oscillated fluid from the feedback system. The outlet channel can include an asymmetric feature to generate acoustic signals detectable in the wellbore.

20 Claims, 9 Drawing Sheets

ASYMMETRIC FLUIDIC OSCILLATOR FOR GENERATING A WELLBORE SIGNAL

TECHNICAL FIELD

The present disclosure relates generally to wellbore operations and, more particularly (although not necessarily exclusively), to an asymmetric fluidic oscillator for generating a signal with respect to a wellbore.

BACKGROUND

A wellbore can be formed in a subterranean formation or a sub-oceanic formation for extracting produced hydrocarbon material. Fluid can be produced from the wellbore. The fluid can include oil, water, gas, other suitable material from the formation, or any combination thereof. Measurements with respect to the fluid can be made to determine information about the fluid. The information can include properties, such as fluid density, amounts of each phase of the fluid, flow rate, and the like. But, measuring the fluid may be difficult. For example, signal strength associated with the fluid may be small and difficult to measure, the combination of phases of the fluid may render the measurements difficult to interpret, and other related difficulties.

DETAILED DESCRIPTION

Certain aspects and examples of the present disclosure relate to an asymmetric fluidic oscillator for generating signals in a wellbore environment. The signals in the wellbore environment may include acoustic signals, seismic waves, pressure waves, or any other suitable signals in the wellbore environment. The signals may be generated via the asymmetric fluidic oscillator. For example, fluid from a wellbore can travel through a flow meter device (e.g., positioned in the wellbore environment) that includes the asymmetric fluidic oscillator. By passing through the asymmetric fluidic oscillator, the fluid may oscillate and generate vibrations or other suitable acoustic signals. The asymmetric fluidic oscillator can include one or more asymmetric features or asymmetric components. For example, the asymmetric fluidic oscillator, or any component thereof such as an outlet channel, may be asymmetric about one or more axes. For example the outlet channel of the asymmetric fluidic oscillator may be asymmetric about an axis that extends along a direction of fluid flow through the asymmetric fluidic oscillator. Additionally, an asymmetric component (e.g., the outlet channel) of the asymmetric fluidic oscillator may be irregularly shaped. For example, the asymmetric component may be an irregular quadrilateral, triangle, pentagon, and the like.

The asymmetry of the fluidic oscillator can facilitate increased vibrations (e.g., increased intensities) or other suitable acoustic signals compared to vibrations or other suitable acoustic signals generated via a symmetric fluidic oscillator with similar fluid. For example, as the fluid oscillates in the asymmetric fluidic oscillator, flow of the fluid may be interrupted or otherwise disrupted. The disrupted flow can be caused by the asymmetric feature or component of the asymmetric fluidic oscillator. For example, an asymmetric outlet channel can interrupt a natural flow of the fluid through the asymmetric fluidic oscillator by redirecting the fluid via the asymmetric feature. The disrupted flow (e.g., the redirected flow of fluid) may cause pressure waves or other suitable types of acoustic signals to be generated by the asymmetric fluidic oscillator. Sensing devices, such as fiber-optic cables, pressure transducers, hydrophones, geophones, accelerometers, differential pressure gauges, other suitable electrical or optical sensing devices, or any combination thereof can detect the acoustic signals generated via the asymmetric fluidic oscillator, and the detected acoustic signals can be used to determine information, such as density, composition, flow, other suitable information, or any combination thereof, relating to the fluid. For example, the asymmetric fluidic oscillator can be interrogated via real-time sensing or data collection tools, memory tools, and the like. Data collected via the interrogation can be converted to flow information, for example, at the surface of the wellbore or in other suitable locations.

A flow meter device can use one or more fluidic oscillators that can each generate an acoustic signal proportional to flow rate and fluid properties of fluid that pass through the fluidic oscillator. Aspects and features of the fluidic oscillator may influence performance of the flow meter device. For example, symmetric fluidic oscillators may not generate acoustic signals with a signal strength large enough to make multi-phase measurements or other suitable measurements relating to fluid produced from a wellbore. And, other flow meter devices may include just one fluidic oscillator, which may not allow multi-phase measurements (e.g., measurements of different phases like water, oil, and gas of the fluid) to be made for the produced fluid.

An asymmetric fluidic oscillator can facilitate signal (e.g., acoustic signal) generation into optical fibers or other suitable measurement devices. The asymmetric fluidic oscillator can facilitate acoustic signal propagation and distributed acoustic sensing (DAS) system data collection in the wellbore environment. For example, the asymmetric fluidic oscillator can cause acoustic signals with higher intensity (compared to signals from symmetric fluidic oscillators) to be generated by similar rates of fluid flow by similar fluid, etc. Additionally, one or more asymmetric fluidic oscillators can be used in a flow meter device to make multi-phase measurements. For example, a first asymmetric fluidic oscillator can be positioned in a first location in the flow meter device, a second asymmetric fluidic oscillator can be positioned in a second location in the flow meter device, and a third asymmetric fluidic oscillator can be positioned in a third location in the flow meter device. Each of the asymmetric fluidic oscillators can be used to make measurements for different phases of the fluid. For example, the first asymmetric fluidic oscillator may be positioned with respect to the flow meter device to measure the water phase of the fluid, the second asymmetric fluidic oscillator may be positioned with respect to the flow meter device to measure the oil phase of the fluid, etc. The asymmetric fluidic oscillators may be otherwise suitably positioned for facilitating multi-phase measurements of the fluid. Additionally, different amounts (e.g., more, such as four, five, six, etc., or fewer, such as one or two) asymmetric fluidic oscillators may be used to facilitate the multi-phase measurements.

The asymmetric fluidic oscillators can generate acoustic signals that propagate to sensing fiber (or other suitable detection devices, such as pressure transducers, etc.) behind or within a casing of a wellbore. In some examples, the signals generated by the asymmetric fluidic oscillator can be detected by one or more DAS systems. Additionally or alternatively to DAS systems, other techniques may be used. The techniques may involve various implementations of Rayleigh scattering, Raman scattering, or Brillouin scattering, and the techniques may be interferometric in nature. The sensing techniques may involve using sensing principles such as homodyne, heterodyne, Michelson, Mach-Zender, Fabry-Perot, phase based, intensity based, coherence based, static (e.g., absolute), or dynamic (e.g., relative). Single-point sensing and multi-point sensing based on Fiber Bragg Gratings or various intrinsic sensing principles or extrinsic sensing principles may also be used in various configurations.

The flow meter device with the asymmetric fluidic oscillator can meter the multi-phase flow through the acoustic signals, such as through a frequency or flow rate relationship. Additionally, analysis of the acoustic signals in the fluid column can be performed and can be used to determine information (e.g., fluid type, flow rate, etc.) relating to the fluid. In some examples, the analysis can involve using Doppler effects, acoustic velocity, dispersion, attenuation or amplitude effects, and the like. Recording and analyzing the acoustic signals with respect to the fluid may involve recording the signal at one or more points upstream from the flow meter device, downstream from the flow meter device, or a combination thereof. Recording and analyzing the acoustic signals can additionally involve array-based acoustic sampling to determine Doppler effects, acoustic velocity, dispersion, amplitude (attenuation) effects, and the like.

Each asymmetric fluidic oscillator that is included in the flow meter device can oscillate at one frequency, which can be a respective fundamental frequency. The asymmetric fluidic oscillator can generate acoustic signals corresponding to the fundamental frequency of the asymmetric fluidic oscillator and associated harmonics. More than one asymmetric fluidic oscillator can be included in a flow meter device, and each asymmetric fluidic oscillator in the flow meter device can correspond to a different fundamental frequencies and associated harmonics.

An asymmetric fluidic oscillator can include an outlet channel with an asymmetry that can cause oscillation (e.g., a variation) in the fluid flow rate through the flow meter device as the fluid oscillates from side to side in the device.

The oscillating flow rate imparts a pressure wave in the inflow of the fluid, the outflow of the fluid, or a combination thereof. A corresponding reaction force can exist through the flow meter device related to this change in pressure and the corresponding change in momentum of the fluid as the flow rate of the fluid through the device oscillates. The oscillating force at the flow meter device can create an enhanced elastic wave, acoustic wave, or equivalently "seismic wave" that can travel in the solid body (e.g., the casing) to which the flow meter device is attached. Thus, enhanced detection of the oscillation signal by a vibrational sensor, a seismic sensor, or a combination thereof that is included in or attached to the associated solid body, offset from the flow meter device is possible. Similarly, an acoustic sensor, a pressure sensor, or a combination thereof located in the flow upstream from the flow meter device or downstream from the flow meter device can detect the pressure wave upstream or downstream of the flow meter device corresponding to the oscillation of the flow of the fluid through the flow meter device.

An asymmetry can be introduced to the fluidic oscillator of the flow meter device such that, as the fluid oscillates within the fluidic oscillator, the flow of the fluid through the flow meter device can be interrupted, which can cause a variation of the flow rate of the fluid through the flow meter device. The variation can impart a force on the flow meter device and a corresponding variation in pressure (e.g., via a pressure wave) upstream of the flow meter device and downstream from the flow meter device. In some examples, the outlet channel of the asymmetric fluidic oscillator can be asymmetric, which can result in an interruption of the flow of the fluid as the fluid oscillates. Pressure waves and elastic waves can be generated upstream and downstream from the asymmetric fluidic oscillator. A pressure sensor located upstream from the asymmetric fluidic oscillator, downstream from the asymmetric fluidic oscillator, or a combination thereof, or a vibration, seismic, optical strain, or strain-rate sensor proximate to the device can detect the pressure waves, the elastic waves, or a combination thereof associated with the flow oscillation. Sensing elements upstream from the asymmetric fluidic oscillator, offset from the asymmetric fluidic oscillator, or a combination thereof can detect an enhanced signal due to the oscillating interruption to the flow of the fluid through the asymmetric fluidic oscillator.

The above illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

Figure 1:
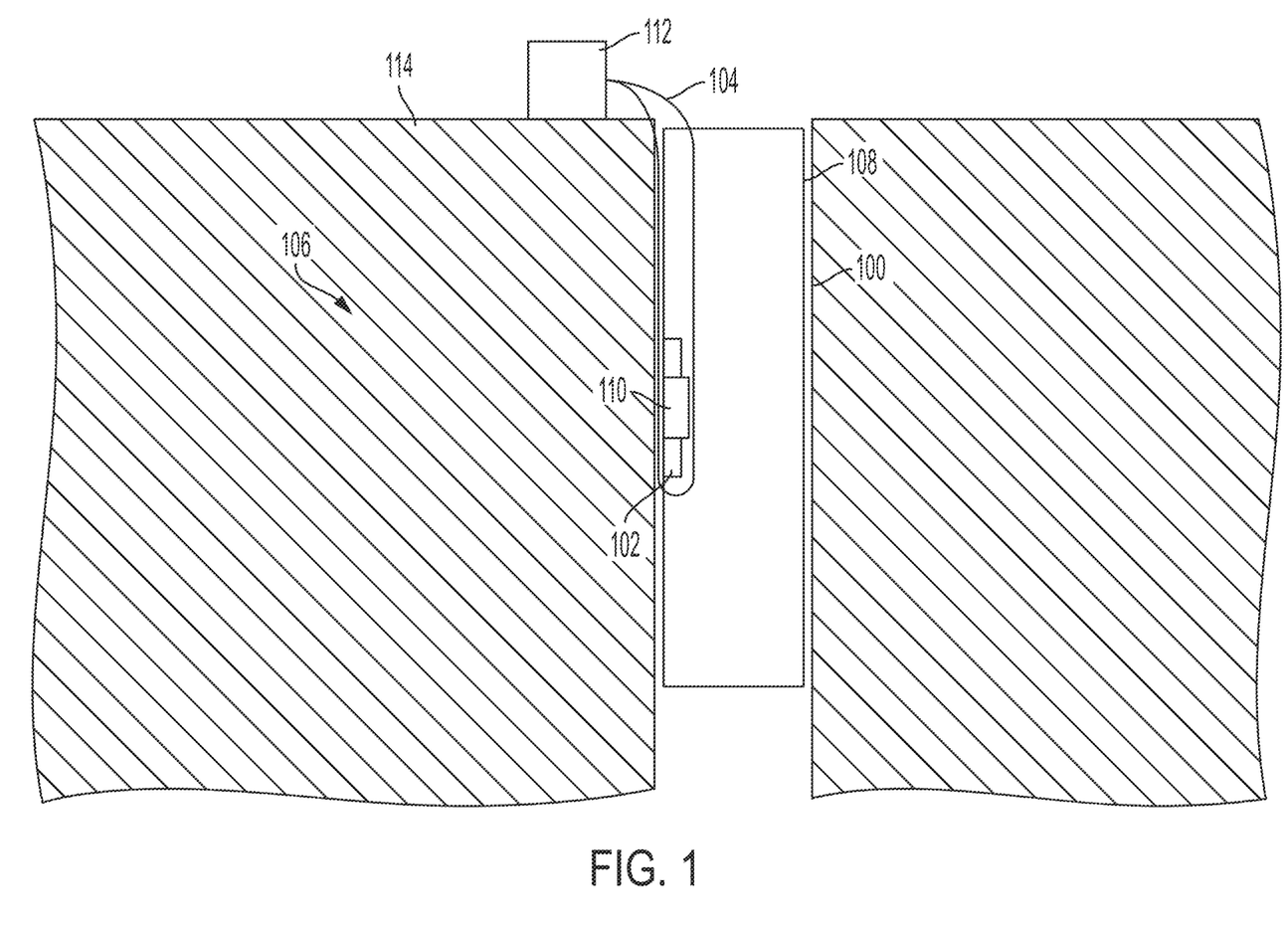
FIG. 1 is a diagram of a wellbore that includes a flow meter device and a measurement device according to one example of the present disclosure.

FIG. 1 is a diagram of a wellbore 100 that includes a flow meter device 102 and a measurement device 104 according to one example of the present disclosure. As illustrated, the wellbore 100 is formed in a subterranean formation 106, but the wellbore 100 can be formed in a sub-oceanic formation or in other suitable locations. As illustrated, the wellbore 100 includes a casing 108, but the wellbore 100 can include a tubing string or other suitable components that facilitate one or more wellbore operations with respect to the wellbore 100. The wellbore 100 can be used to produce fluid from the subterranean formation 106. For example, the wellbore 100 can be used to extract water, oil, gas, other suitable fluid or material, or any combination thereof from the subterranean formation 106.

The flow meter device 102 can be positioned in the wellbore 100. For example, the flow meter device 102 can be affixed to, or otherwise positioned in, the casing 108 of the wellbore 100. The flow meter device 102 can be positioned in any other suitable location (e.g., at the surface, etc.) with respect to the wellbore 100 for measuring properties related to the fluid produced from the wellbore 100. The fluid can travel through the flow meter device 102, and the flow meter device 102 can generate, or otherwise facilitate any sub-component to generate, acoustic waves.

In some examples, the flow meter device 102 can include an acoustic device 110. The acoustic device 110 can include a fluidic oscillator, a hole-turn whistle, and the like. In some examples, the acoustic device 110 can be an asymmetric fluidic oscillator. For example, at least one component (e.g., an inlet channel, an outlet channel, a feedback system, etc.) of the asymmetric fluidic oscillator may be asymmetric. The asymmetry of the fluidic oscillator may cause larger, or otherwise easier-to-detect, acoustic waves (compared to waves generated by other acoustic devices) to be generated by the flow of similar fluids.

The flow meter device 102 can include one or more acoustic devices 110 such as the asymmetric fluidic oscillator. For example, the flow meter device 102 can include one, two, three, four, or more asymmetric fluidic oscillators. The flow meter device 102 can include an amount of asymmetric fluidic oscillators corresponding to an amount of phases included or expected to be in fluid produced via the wellbore 100. For example, if the fluid includes or is expected to include three phases corresponding to oil, gas, and water, then the flow meter device 102 can include three asymmetric fluidic oscillators to perform a multi-phase measurement of the fluid. In such an example, the three asymmetric fluidic oscillators may be positioned in different locations (e.g., around a circumference of the flow meter device 102, etc.) with respect to the flow meter device 102. Additionally or alternatively, more than one flow meter device 102 can be included in the wellbore 100 to perform the multi-phase measurement of the fluid. For example, if the fluid includes or is expected to include three phases, then three different flow meter devices can be included in the wellbore 100. The three different flow meter devices can be positioned a minimum distance apart and each may include a different asymmetric fluidic oscillator for measuring a different phase of the fluid.

The measurement device 104 may include one or more fiber optic cables cemented in place in the annular space between the casing 108 and the subterranean formation 106. The measurement device 104 may be interrogated to measure signals generated by the acoustic devices 110 such as fluidic oscillators. The measurement device 104 may be clamped to the outside of the casing 108 during the deployment and protected by centralizers or cross coupling clamps during run-in-hole. Other applications include tubing-conveyed cables or retrievable sensing cables like wireline and slickline, or cables deployed inside coiled tubing. The measurement device 104 may also be deployed in the wellbore 100 using gravity such that a weight or conveyance vehicle is dropped into the wellbore 100, and the measurement device 104 is released in the wellbore 100 as the deployment vehicle proceeds in the wellbore 100. The measurement device 104 may be payed out from the surface or from a coil in the deployment vehicle.

Other examples of the measurement device 104 may include point sensors either at the surface, down-hole, or a combination thereof. In some examples, single-point or multi-point pressure or temperature sensors can be used in reservoir monitoring applications in which the pressure sensors may collect data at rates up to 2,000 Hz or even higher.

The measurement device 104 may house one or more optical fibers, and the optical fibers may be single-mode fibers, multi-mode fibers, or a combination thereof. The measurement device 104 connected to the optical fibers may include distributed temperature sensing (DTS) systems, DAS systems, distributed strain sensing (DSS) systems, quasi-distributed sensing systems in which multiple single-point sensors are distributed along an optical fiber or cable, or single-point sensing systems in which the sensors are located at the end of the cable.

The measurement device 104 may operate using various sensing principles, such as Rayleigh scattering, Brillouin scattering, and Raman scattering. For example, the sensing principles can include (i) amplitude-based sensing systems, such as DTS systems based on Raman scattering, and (ii) phase-sensing-based systems, such as DAS systems based on interferometric sensing using homodyne or heterodyne techniques in which the system may sense phase or intensity changes due to constructive or destructive interference. The sensing principles can additionally include (iii) strain-sensing systems like DSS using dynamic strain measurements based on interferometric sensors or static strain sensing measurements using Brillouin scattering, quasi-distributed sensors based on Fiber Bragg Gratings (FBGs) in which a wavelength shift is detected, etc. In some examples, multiple FBGs can be used to form Fabry-Perot-type interferometric sensors for phase-based or intensity-based sensing.

True, distributed fiber-optic-sensing systems, such as one example of the measurement device 104, may operate using optical time domain reflectometry principles or optical frequency domain reflectometry. Optical time domain reflectometry-based systems can be pulsed such that one or more optical pulses may be transmitted down an optical fiber of the measurement device 104 and backscattered light, such as Rayleigh, Brillouin, Raman, etc., can be measured and processed. Time of flight for the optical pulses can indicate a location along the optical fiber the measurement is made. Optical frequency domain reflectometry-based systems can operate in a continuous-wave mode in which a tunable laser is swept across a wavelength range, and the back scattered light is collected and processed.

Various hybrid approaches, in which single-point, quasi-distributed, or distributed fiber optic sensors of the measurement device 104 can be mixed with electrical sensors, can be used. The measurement device 104 may include optical fiber and electrical conductors. Electrical sensors may be pressure sensors based on quartz-type sensors, strain-gauge-based sensors, etc. Pressure sensors, optical sensors, or electrical sensors may be housed in dedicated gauge mandrels or attached outside the casing 108 in some examples for down-hole deployment or for conventional deployment at the surface of the wellbore 100.

Temperature measurements from a DTS system may be used to determine locations for water injection applications where fluid inflow in the treatment well as the fluids from the surface may be cooler than formation temperatures. Temperature measurements in observation wells can be used to determine fluid communication between the treatment well and observation well, or to determine formation fluid movement. DAS data can be used to determine fluid allocation in real-time as acoustic signals are generated when fluid flows, for example through the flow meter device 102. Phase-based and intensity-based interferometric sensing systems can be sensitive to temperature, mechanical vibrations, and acoustically-induced vibrations. DAS data can be converted from time-series data to frequency-domain data using Fast Fourier Transforms and other transforms like wavelet transforms.

Various frequency ranges can be used with respect to the measurement device 104, for example in which low frequency signal changes may be attributed to formation strain changes or temperature changes due to fluid movement, etc. Various filtering techniques and models may be applied to generate indicators of events that may be of interest. Indicators may include formation movement due to growing natural fractures, formation stress changes during the fracturing operations (stress shadowing), etc. Each indicator may include a characteristic signature such as frequency content, amplitude, or time dependent behavior, etc. The indicators may also be present in other data types and may not be limited to DAS data. Fiber optic cables used with DAS systems, such as the measurement device 104, may include enhanced backscatter optical fibers where the Rayleigh backscatter may be increased by 10 times or more with an associated increase in optical signal-to-noise ratio.

DAS systems, such as one example of the measurement device 104, can also be used to detect various seismic events where stress fields or growing fracture networks can generate microseismic events or where perforation charge events may be used to determine travel time between horizontal wells. The detected data can be used to determine changes in travel time as the formation is fractured and filled with fluid, proppant, etc. The DAS systems may also be used with surface seismic sources to generate vertical seismic profiles before, during, and after a fracturing operation to determine the effectiveness of the fracturing operation and to determine production effectiveness and perform other tasks relating to other wellbore operations.

DSS data, such as one example of data generated or detected via the measurement device 104, can be generated using various approaches. Static strain data can be used to determine absolute strain changes over time. Static strain data can be measured using Brillouin-based systems or quasi-distributed strain data. Static strain may be used to determine propped fracture volume by determining deviations in strain data from a measured strain baseline before fracturing a stage. Formation properties, such as permeability, poro-elastic responses, and leak-off rates, can be determined based on the change of strain vs. time and the rate at which the strain changes over time. Dynamic strain data can be used in real-time to detect fracture growth through an appropriate inversion model, and appropriate actions like dynamic changes to fluid flow rates in the treatment well, addition of diverters or chemicals into the fracturing fluid, or changes to proppant concentrations or types can be used.

The measurement device 104 can be placed in either a treatment well or one or more monitoring wells to measure well communication. The treatment well pressure, rate, proppant concentration, diverters, fluids, chemicals, etc. may be altered to control a wellbore operation. The changes may impact the formation responses in various ways. For example, stress fields may change, which may generate microseismic effects that can be measured with DAS systems or single-point seismic sensors like geophones. Additionally, pressure changes due to poro-elastic effects may be measured in the monitoring well. And, pressure data may be measured in the treatment well and correlated to formation responses.

The measurement device 104 can be used to detect the acoustic signals emitted from or generated by the flow meter device 102. As illustrated, the measurement device 104 is a fiber-optic cable, but other types of measurement devices 104, such as pressure transducers and the like, are possible. The measurement device 104 can be communicatively coupled to a detection system 112. The detection system 112 can be positioned at a surface 114 of the wellbore 100 or in other suitable locations (e.g., in the wellbore 100, remote from the wellbore 100, etc.) with respect to the wellbore 100. The measurement device 104 can be connected to the detection system 112 via a wired connection, a wireless connection, or a combination thereof. In some examples, the detection system 112 can include a DAS system, a computing system configured to receive, record, or analyze the acoustic signals, other suitable detection systems, or any combination thereof.

Fluid produced via the wellbore 100 can travel or can otherwise be forced or directed through the flow meter device 102 that includes the acoustic device 110 (e.g., the asymmetric fluidic oscillator). The fluid can oscillate in the asymmetric fluidic oscillator, which can generate or propagate acoustic signals. The acoustic signals can be detected using the measurement device 104, which can capture the acoustic signals and transmit a subsequent signal to the detection system 112. The signals can be used by the detection system 112, or other suitable component or computing system, to determine information relating to the fluid. The information can include a flow rate, a fluid composition, a fluid density, and the like.

Figure 2:
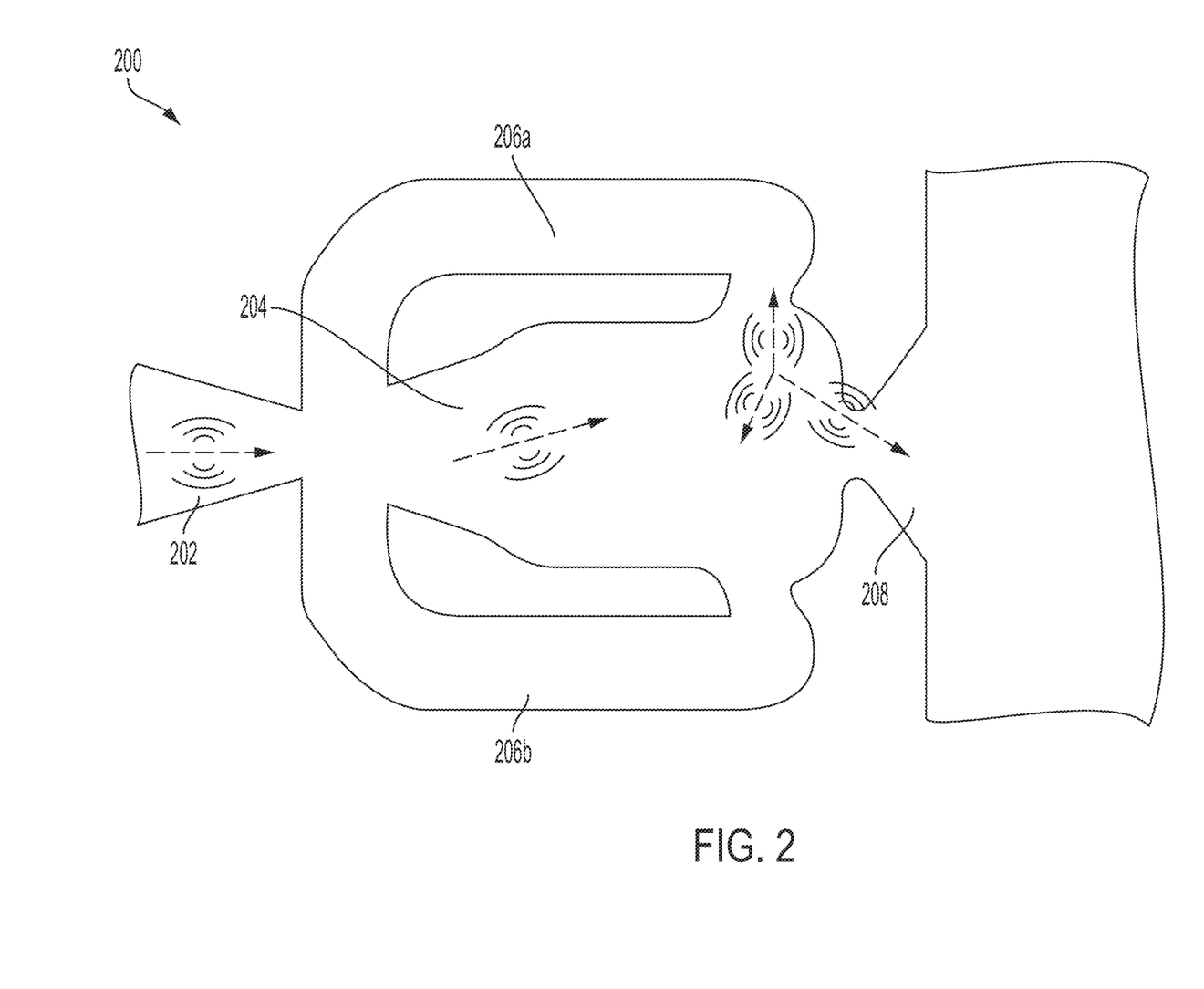
FIG. 2 is a diagram of a fluid flow with respect to a fluidic oscillator according to one example of the present disclosure.

FIG. 2 is a diagram of a fluid flow with respect to a fluidic oscillator 200 according to one example of the present disclosure. The fluidic oscillator can include an inlet channel 202, a mixing chamber 204, feedback loops 206a-b, and an outlet channel 208. The inlet channel 202 may be coupled to the mixing chamber 204, which may be coupled to the feedback loops 206a-b and the outlet channel 208. The fluidic oscillator 200 can include other or different suitable components. Additionally, while illustrated as symmetric, the fluidic oscillator 200 may be asymmetric or otherwise include an asymmetric feature (e.g., the outlet channel 208 or other suitable feature of the fluidic oscillator 200 may be asymmetric).

Fluid may be directed into the fluidic oscillator 200 via the inlet channel 202. The fluid may travel into the mixing chamber 204, and the fluid may oscillate (e.g., in the mixing chamber 204, by traveling through one or more of the feedback loops 206a-b, by flowing through the outlet channel 208, etc.). The frequency of oscillation of the fluid may depend on various factors. For example, the frequency of oscillation of the fluid can be a linear function of the flow rate of the fluid. Additionally or alternatively, the frequency of oscillation of the fluid may depend on pressure drop (e.g., the square root of the pressure drop) in the fluidic oscillator 200. The frequency of oscillation may depend on other suitable factors relating to the fluidic oscillator 200. In some examples, the oscillation of the fluid in the fluidic oscillator 200 may cause acoustic signals to be generated. Acoustic signals generated from other fluidic oscillators (e.g., symmetric fluidic oscillators, etc.) may not include an intensity large enough to be detected with respect to the wellbore 100. Accordingly, the fluidic oscillator 200 may be asymmetric to generate acoustic signals with increased intensity compared to the other fluidic oscillators.

Figure 3:
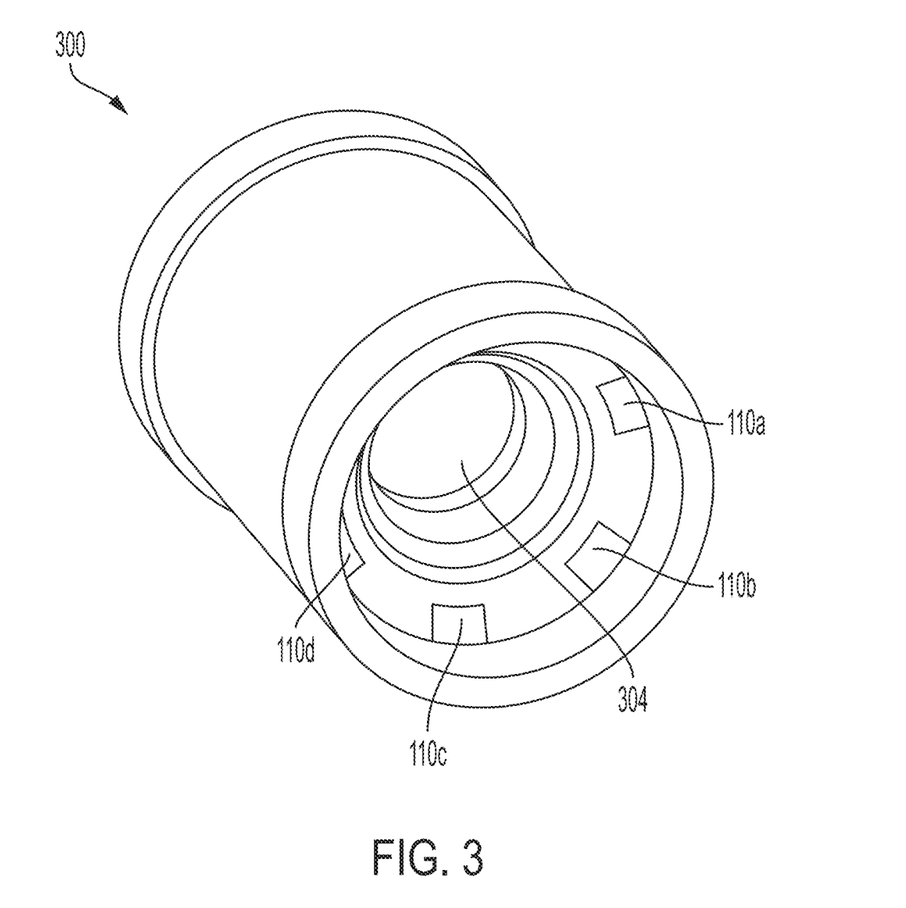
FIG. 3 is a perspective view of a flow meter device according to one example of the present disclosure.

FIG. 3 is a perspective view of a flow meter device 102 according to one example of the present disclosure. The flow meter device 102 can be positioned in the wellbore 100, at the surface 114 of the wellbore 100, or in other suitable locations. In some examples, the flow meter device 102 can be positioned in the casing 108 or other suitable flow line of the wellbore 100. The flow meter device 102 can be used to determine flow rate and other information relating to fluid flowing with respect to the wellbore 100. The flow meter device 102 can include a set of acoustic devices 110a-d and a bore hole 304. While illustrated with four acoustic device 110a-d, the flow meter device 102 can include other suitable amounts (e.g., less than four or more than four) of acoustic devices 110. The flow meter device 102 can include any other suitable components.

The flow meter device 102 can include an amount of acoustic devices 110 that corresponds to an amount of phases of fluid from the wellbore 100. For example, if the fluid includes four phases, then the flow meter device 102 can include (e.g., as illustrated) four acoustic devices 110. As illustrated, the acoustic devices 110a-d are positioned near the circumference of the flow meter device 102, but the acoustic devices 110a-d can be positioned in other suitable locations with respect to the flow meter device 102. The acoustic devices 110a-d can be positioned to detect or otherwise sense data relating to one or more phases of the fluid. For example, the acoustic device 110a may be positioned to sense data about a gas phase of the fluid, the acoustic device 110b may be positioned to sense data about a combination oil/gas phase of the fluid, the acoustic device 110c may be positioned to sense data about a water phase of the fluid, etc. The bore hole 304 may be positioned in (or approximately in) the center of the flow meter device 102. The size of the bore hole 304, the shape of the bore hole 304, or a combination thereof can be selected based on expected fluid properties, the acoustic device 110 type or placement, desired measurements, other suitable parameters, or any combination thereof. In some examples, the bore hole 304 may be omitted.

Figure 4:
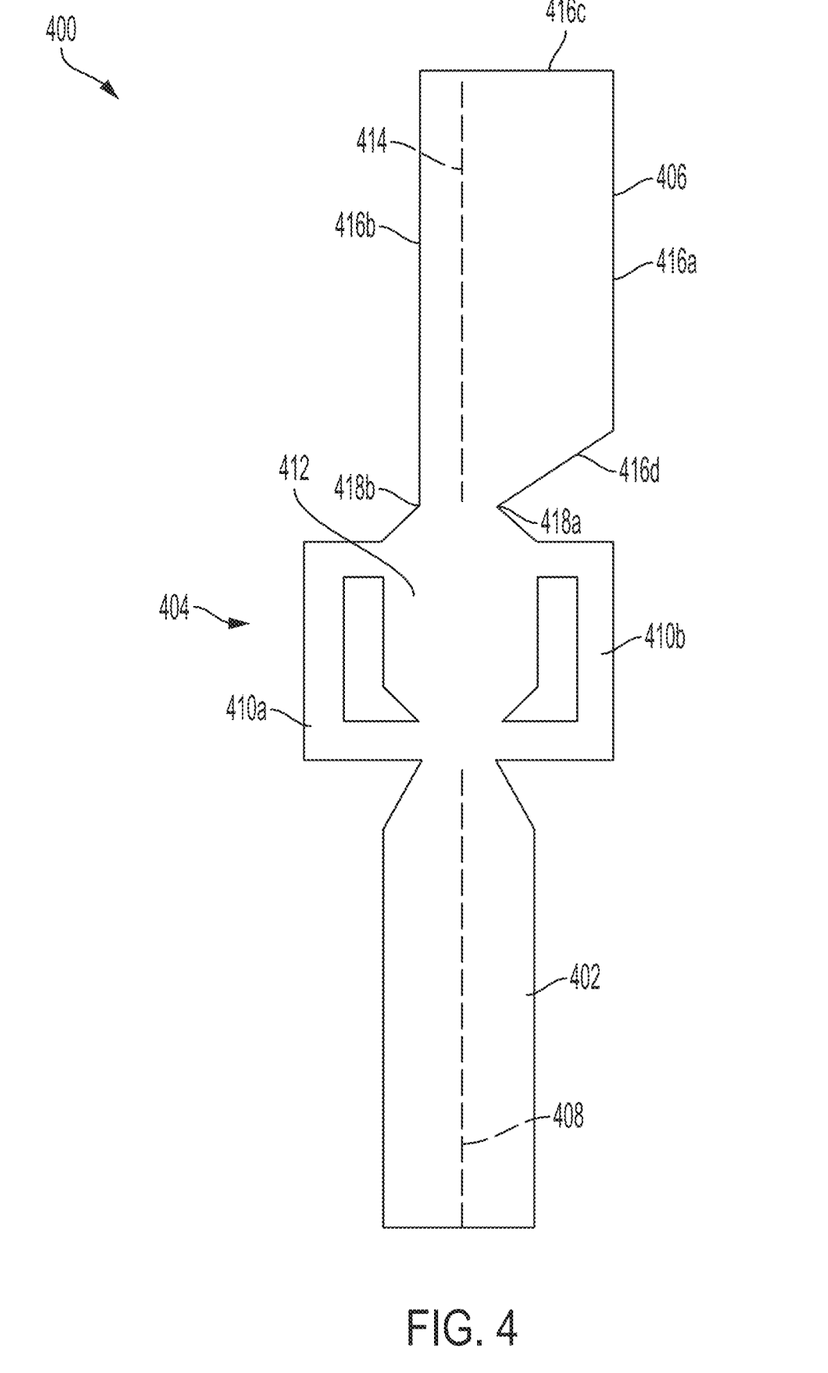
FIG. 4 is a diagram of one example of an asymmetric fluidic oscillator according to one example of the present disclosure.

FIG. 4 is a diagram of an asymmetric fluidic oscillator 400 according to one example of the present disclosure. The asymmetric fluidic oscillator 400 can include an inlet channel 402, a feedback system 404, an outlet channel 406, and any other suitable components. The asymmetric fluidic oscillator 400 can be included in the flow meter device 102 and may cause acoustic signals to be generated via oscillating fluid flow in the asymmetric fluidic oscillator 400.

The inlet channel 402 may include a receiving path in the asymmetric fluidic oscillator 400. For example, the inlet channel 402 can receive fluid (e.g., from the casing 108 or other suitable components of the wellbore 100) that may originate upstream from the asymmetric fluidic oscillator 400, and the inlet channel 402 can direct the fluid further into the asymmetric fluidic oscillator 400 such as into the feedback system 404. The inlet channel 402 can be symmetric or asymmetric. As illustrated in FIG. 4, the inlet channel 402 is symmetric about axis 408, but the inlet channel 402 may be symmetric about other suitable axes or may be asymmetric.

As illustrated, the feedback system 404 is coupled (e.g., mechanically) to the inlet channel 402 and the outlet channel 406. Additionally or alternatively, the feedback system 404 can be coupled to other suitable components of the asymmetric fluidic oscillator 400. As illustrated, the feedback system 404 includes a first feedback loop 410a, a second feedback loop 410b, and a mixing chamber 412. The feedback system 404 can include any other suitable components and may be otherwise suitable shaped or configured. For example, the feedback system 404 can include more or fewer feedback loops 410, a differently sized or shaped mixing chamber 412, differently shaped or sized feedback loops 410, etc. for oscillating the fluid.

The outlet channel 406 can be coupled (e.g., mechanically) to the feedback system 404. For example, the outlet channel 406 can be coupled to the feedback loops 410a-b, the mixing chamber 412, to other suitable components, or to any suitable combination thereof. The outlet channel 406 may define an exit path for fluid received from the feedback system 404. For example, fluid may be received from the feedback system 404 by the outlet channel 406, and the outlet channel 406 may direct the fluid out (e.g., into the casing 108 of the wellbore 100 or other suitable component thereof) of the asymmetric fluidic oscillator 400.

The outlet channel 406 may be asymmetric. For example, the outlet channel 406 may not be symmetric along any suitable axes of the outlet channel 406. As illustrated, the outlet channel 406 is not symmetric about axis 414, which may be similar or identical to the axis 408 of the inlet channel 402. The asymmetric nature of the outlet channel 406 may cause disruptions or other suitable variations in the flow of fluid that passes through the outlet channel 406. For example, the asymmetry of the outlet channel 406 may interrupt the natural flow of the fluid, and the interruption may cause vibrations or other suitable acoustic signals that may be larger or that otherwise may include higher intensities than signals produced from symmetric fluidic oscillators.

As illustrated in FIG. 4, the outlet channel 406 is an irregularly shaped quadrilateral. But, the outlet channel 406 can be or otherwise include any other suitable irregular or asymmetric shapes (e.g., an irregular pentagon, a regular quadrilateral having jagged edges, etc.). The outlet channel 406 can include a right side 416a, a left side 416b, a top side 416c, and a bottom side 416d. The right side 416a may be connected to the bottom side 416d and to the top side 416c, the left side 416b may be connected to the top side 416c and to the feedback system 404, and the bottom side 416d may be connected to the feedback system 404. The right side 416a and the left side 416b may be substantially parallel to one another. In other examples, the right side 416a and the left side 416b may be non-parallel. Additionally, the top side 416c and the bottom side 416d may be non-parallel for forming the asymmetric feature of the outlet channel 406. In some examples, the asymmetric feature can be formed via the bottom side 416d coupling to the feedback system 404 in a first location 418a, while the left side 416b is coupled in a second location 418b to the feedback system 404. Accordingly, the right side 416a may be shorter than the left side 416b, and the bottom side 416d may include a defined and non-zero slope.

Fluid received by the inlet channel 402 can be directed to the feedback system 404. For example, the inlet channel 402 can receive produced fluid from the wellbore 100 and can direct the produced fluid to the feedback system 404. The produced fluid can enter the feedback system 404 (e.g., via the feedback loops 410a-b, the mixing chamber 412, or a combination thereof) and can oscillate or otherwise suitably flow. For example, the produced fluid can travel through the first feedback loop 410a or the second feedback loop 410b and into the mixing chamber 412 (e.g., via one or more iterations). The produced fluid may be directed into the outlet channel 406. The asymmetric nature of outlet channel 406 may cause disruption of flow of the produced fluid through the outlet channel 406. The disruption may propagate from the outlet channel 406 to the feedback system 404 or to other suitable components of the asymmetric fluidic oscillator 400 or of the wellbore 100. The disruption in the flow of the produced fluid can cause vibrations or other suitable acoustic signals to be generated. The acoustic signals generated via the disruption may include a periodicity that is different than non-disrupted flow and may include an intensity that is higher than an intensity of signals generated via symmetric fluidic oscillators or other types of acoustic devices. Accordingly, the measurement device 104 may be able to detect, or otherwise be used to detect, the acoustic signals generated via the disruption.

Figure 5:
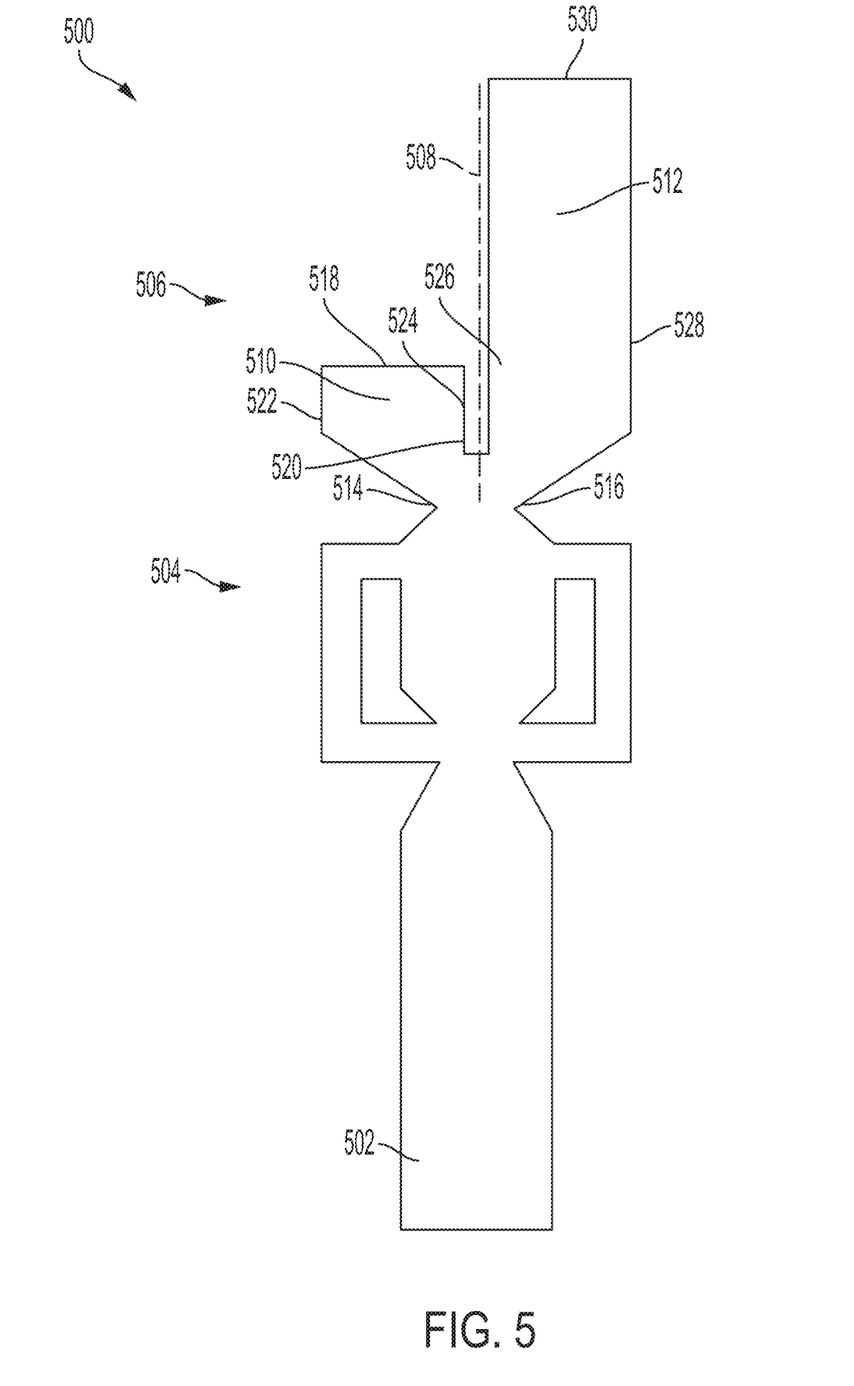
FIG. 5 is a diagram of another example of an asymmetric fluidic oscillator according to one example of the present disclosure.

FIG. 5 is a diagram of another example of an asymmetric fluidic oscillator 500 according to one example of the present disclosure. The asymmetric fluidic oscillator 500 can include an inlet channel 502, a feedback system 504, and an outlet channel 506. As illustrated, the inlet channel 502 is similar to the inlet channel 402, and the feedback system 504 is similar to the feedback system 404. But, the inlet channel 502, the feedback system 504, or a combination thereof may differ from corresponding features of the asymmetric fluidic oscillator 400. The asymmetric fluidic oscillator 500 can be included in the flow meter device 102 and may cause acoustic signals to be generated via oscillating fluid flow in the asymmetric fluidic oscillator 500.

The inlet channel 502 may be coupled (e.g., mechanically) to the feedback system 504, which may, in turn, be coupled to the outlet channel 506. The outlet channel 506 may be asymmetric. For example, the outlet channel 506 may not include any axes about which the outlet channel 506 is symmetric. In some examples, the outlet channel 506 may be asymmetric about axis 508, which may extend along a flow direction of fluid through the asymmetric fluidic oscillator 500.

The outlet channel 506 may include a first portion 510 and a second portion 512 and, optionally, other portions for disrupting flow of fluid through the asymmetric fluidic oscillator 500 to generate acoustic signals. The first portion 510 may be coupled (e.g., mechanically) to the feedback system 504 at a first location 514, and the second portion 512 may be coupled to the feedback system 504 at a second location 516, which may be different than the first location 514. The second portion 512 may allow flow of fluid through the asymmetric fluidic oscillator 500. But, the first portion 510 may not allow flow of fluid through the asymmetric fluidic oscillator 500. For example, the first portion 510 may include a cap 518 or may otherwise be blocked so that fluid may not exit through the outlet channel 506 via the first portion 510. Accordingly, fluid flow through the outlet channel 506 may be disrupted, and vibrations or acoustic signals can be generated based on the disrupted flow of the fluid.

As illustrated, the outlet channel 506 includes the first portion 510 and the second portion 512 that are separated by buffer 520. The first portion 510 and the second portion 512 may include differing measurements or features. For example, a left side 522 of the first portion 510 and a right side 524 of the first portion 510 may be shorter or otherwise smaller than a left side 526 of the second portion 512 and the right side 528 of the second portion 512, respectively. Additionally, the cap 518 of the first portion may restrict or otherwise prevent flow of fluid through the outlet channel 506 via the first portion 510, while a top 530 of the second portion 512 may be open or otherwise allow flow of the fluid through the outlet channel 506 via the second portion 512. In some examples, the first portion 510 may allow flow, while the second portion 512 restricts or obstructs the flow. The outlet channel 506 can include other suitable amounts of portions, which can include other suitable features or measurements, with sufficient asymmetry to produce the acoustic signals.

Figure 6:
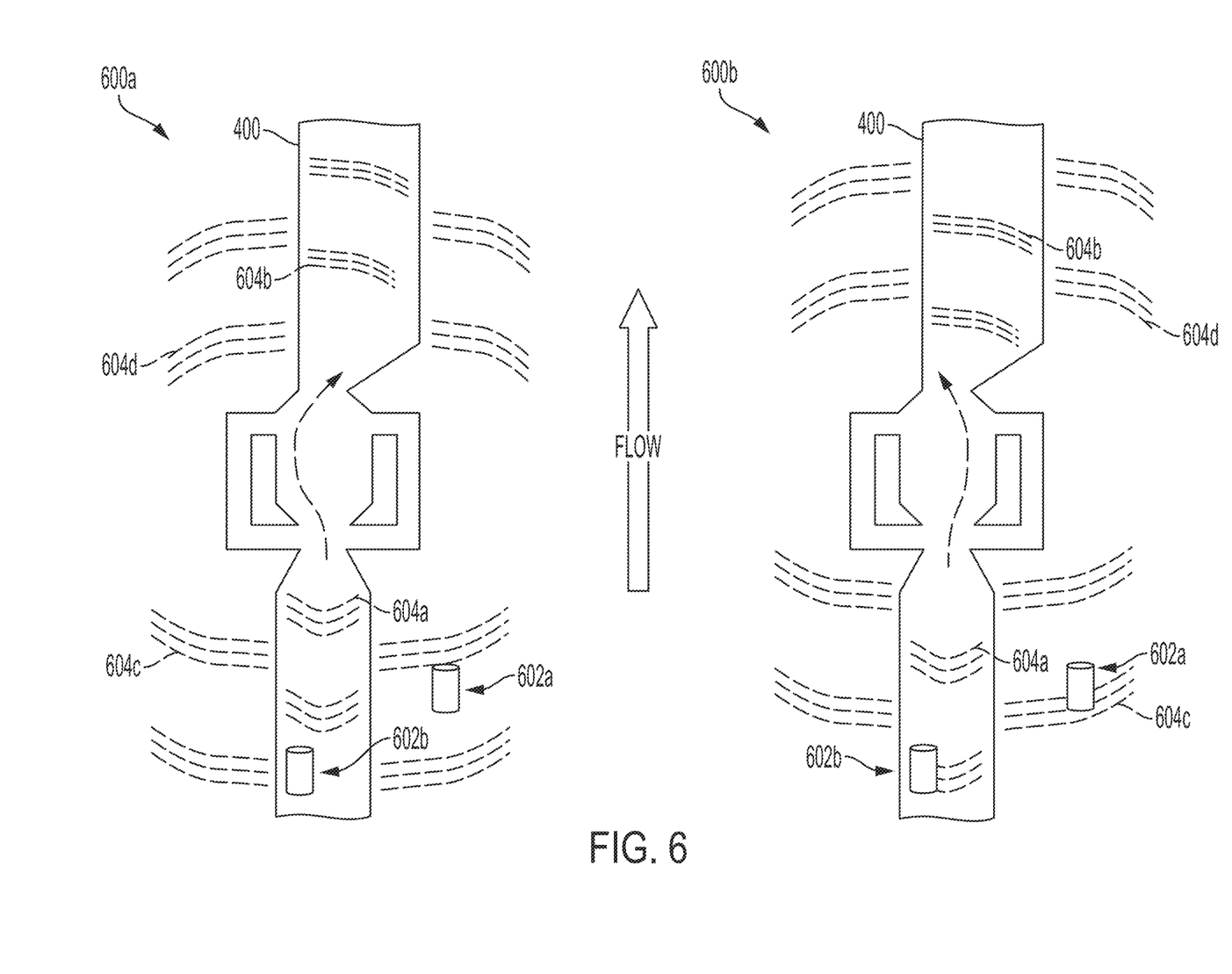
FIG. 6 is a diagram of an example of oscillating fluid in an asymmetric fluidic oscillator according to one example of the present disclosure.

FIG. 6 is a diagram of an example of oscillating fluid in an asymmetric fluidic oscillator 400 according to one example of the present disclosure. FIG. 6 illustrates a first stage 600*a* of fluid flow and a second stage 600*b* of fluid flow, but other suitable stages of fluid flow are possible. The stages 600*a-b* include acoustic waves 604*a-b* within the asymmetric fluidic oscillator 400 and acoustic waves 604*c-d* external to the asymmetric fluidic oscillator 400.

The first stage 600*a* involves fluid (e.g., produced from the wellbore 100) flowing through the asymmetric fluidic oscillator 400 in a first stage of oscillation, which can involve the fluid oscillating or otherwise bouncing against a left side of the asymmetric fluidic oscillator 400. The fluid may produce the acoustic waves 604*a-d*. The acoustic waves 604*a* within the asymmetric fluidic oscillator 400 may lag behind the acoustic waves 604*c*, which are external with respect to the asymmetric fluidic oscillator 400, upstream from the asymmetric fluidic oscillator 400. The acoustic waves 604*b* within the asymmetric fluidic oscillator 400 may propagate ahead of the acoustic waves 604*d*, which are external with respect to the asymmetric fluidic oscillator 400, downstream from the asymmetric fluidic oscillator 400.

The sensors 602*a-b* may be positioned upstream from the asymmetric fluidic oscillator 400. For example, the sensor 602*a* can be positioned upstream and external from the asymmetric fluidic oscillator 400. Additionally, the sensor 602*b* can be positioned upstream and internal with respect to the asymmetric fluidic oscillator 400. The sensors 602*a-b* can include a fiber-optic cable, a pressure transducer, a geophone, and the like that can detect or transmit acoustic signals (e.g., generated via the asymmetric fluidic oscillator 400). For example, the sensor 602*a* can detect the acoustic waves 604*c*, and the sensor 602*b* can detect the acoustic waves 604*a*. As illustrated in FIG. 6, the acoustic waves 604*c* may be detected by the sensor 602*a* prior to the sensor 602*b* detecting the acoustic waves 604*a* since flow of fluid through the asymmetric fluidic oscillator 400 is disrupted. In some examples, the acoustic waves 604*c* may be detected by the sensor 602*a* in other temporal relationships with respect to the sensor 602*b* detecting the acoustic waves 604*a*.

The second stage 600*b* involves fluid (e.g., produced from the wellbore 100) flowing through the asymmetric fluidic oscillator 400 in a second stage of oscillation, which may be different than the first stage of oscillation and can involve the fluid oscillating or otherwise bouncing against a right side of the asymmetric fluidic oscillator 400. The fluid may produce or otherwise further propagate the acoustic waves 604*a-d*. For example, by continuously oscillating the fluid, the asymmetric fluidic oscillator 400 may continuously generate the acoustic waves 604*a-d*, may propagate the acoustic waves 604*a-d* further from a central point of the asymmetric fluidic oscillator 400, or a combination thereof.

Figure 7:
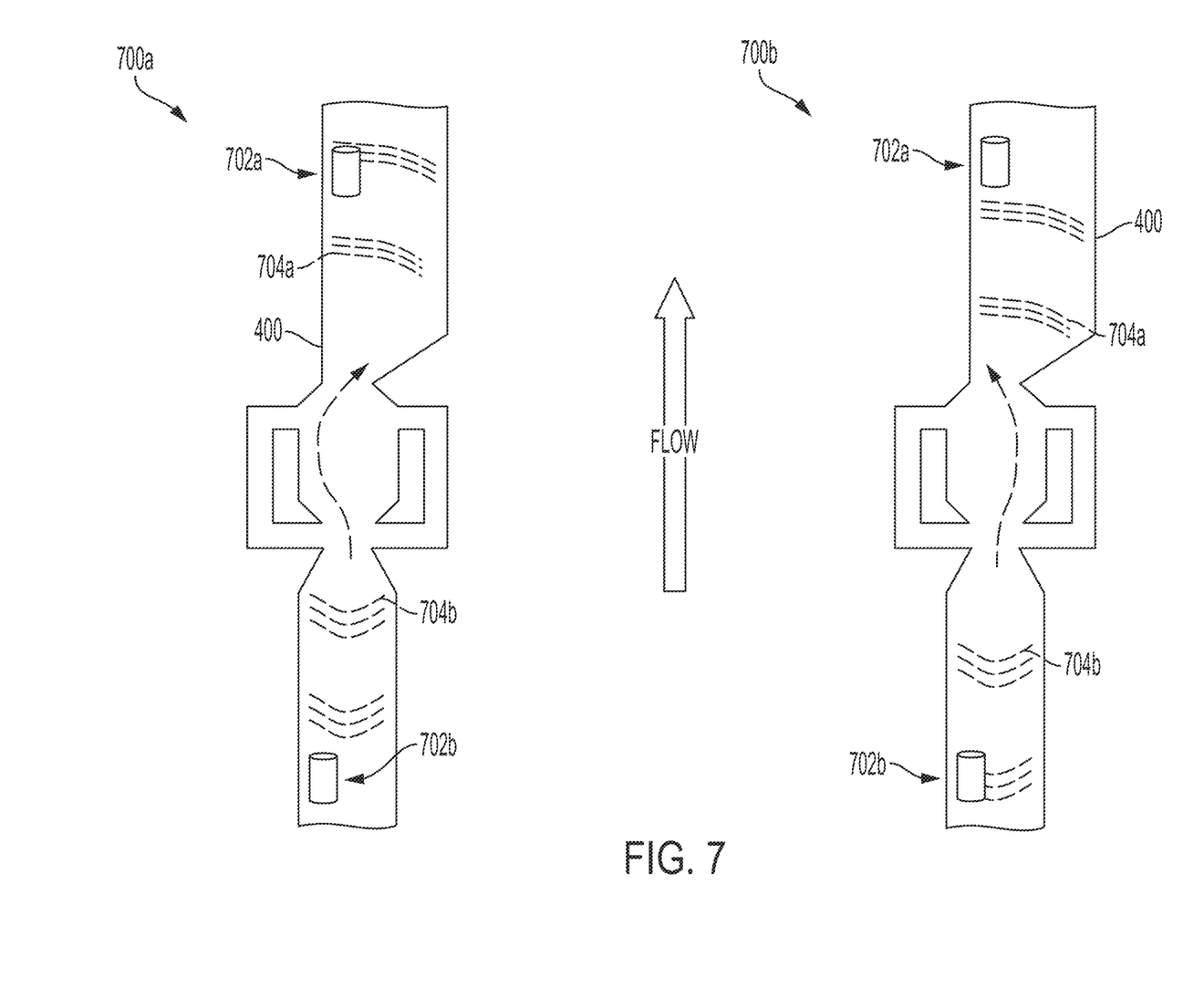
FIG. 7 is a diagram of another example of oscillating fluid in an asymmetric fluidic oscillator according to one example of the present disclosure.

FIG. 7 is a diagram of another example of oscillating fluid in an asymmetric fluidic oscillator 400 according to one example of the present disclosure. The sensors 702*a-b* may include fiber-optic cables, pressure transducers, or other suitable measurement devices that can detect acoustic signals generated via the asymmetric fluidic oscillator 400. FIG. 7 illustrates a first stage 700*a* of fluid flow and a second stage 700*b* of fluid flow, but other suitable stages of fluid flow are possible with the asymmetric fluidic oscillator 400.

In some examples, the first stage 700*a* and the second stage 700*b* can each involve a disruption (e.g., based on the asymmetry of the asymmetric fluidic oscillator 400) to the flow of fluid through the asymmetric fluidic oscillator 400. The disruption of the flow of fluid can cause acoustic waves 704a-b to be generated. The acoustic waves 704a can travel in a downstream direction with respect to the asymmetric fluidic oscillator 400, and the acoustic waves 704b can travel in an upstream direction with respect to the asymmetric fluidic oscillator 400. The acoustic waves 704a can be detected by the sensor 702a, which can be positioned downstream with respect to the asymmetric fluidic oscillator 400. The acoustic waves 704b can be detected by the sensor 702b, which can be positioned upstream with respect to the asymmetric fluidic oscillator 400. As illustrated, the sensors 702a-b are positioned in components of the asymmetric fluidic oscillator 400, but the sensors 702a-b may be positioned externally with respect to the asymmetric fluidic oscillator 400. In some examples, the signals detected by the sensors 702a-b can be used to determine a differential acoustic signal that can be used to determine information (e.g., flow rate, fluid density, etc.) about the fluid flowing through the asymmetric fluidic oscillator 400.

The first stage 700a can involve fluid (e.g., fluid produced from the wellbore 100) travelling through the asymmetric fluidic oscillator 400 and oscillating or otherwise bouncing off of a left side of the asymmetric fluidic oscillator 400. The first stage 700a can involve disruption of the fluid flowing through the asymmetric fluidic oscillator 400. The second stage 700b can involve fluid (e.g., fluid produced from the wellbore 100) travelling through the asymmetric fluidic oscillator 400 and oscillating or otherwise bouncing off of a right side of the asymmetric fluidic oscillator 400. The second stage 700b can involve the disruption of the fluid flowing through the asymmetric fluidic oscillator 400. In some examples, the disruption may involve an interruption of flow of the fluid while the fluid oscillates in the asymmetric fluidic oscillator 400. Pressure waves or other suitable waves or signals can be generated and may propagate (e.g., upstream and downstream with respect to the asymmetric fluidic oscillator 400) from the asymmetric fluidic oscillator 400. The sensors 702a-b can detect the waves or signals generated via the interruption of fluid flow.

Figure 8:
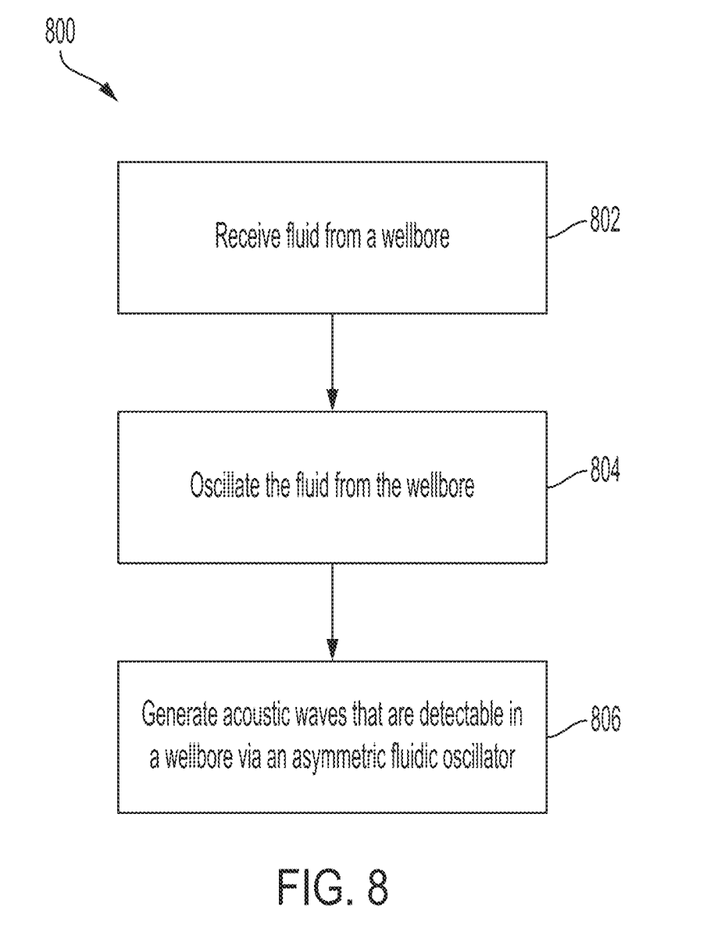
FIG. 8 is a flow chart of a process for generating acoustic signals using an asymmetric fluidic oscillator according to one example of the present disclosure.

FIG. 8 is a flow chart of a process 800 for generating acoustic signals using an asymmetric fluidic oscillator 400 according to one example of the present disclosure. At block 802, the asymmetric fluidic oscillator 400 receives fluid from a wellbore 100. The asymmetric fluidic oscillator 400 can be positioned in a flow meter device 102 in the wellbore 100 and can include an inlet channel 402, a feedback system 404, and an outlet channel 406 that can be asymmetric or otherwise include an asymmetric feature. The asymmetric fluidic oscillator 400 can receive the fluid from the wellbore 100 via the inlet channel 402 or other suitable component of the asymmetric fluidic oscillator 400. The fluid from the wellbore 100 can include a single-phase fluid or a multi-phase fluid. For example, the fluid from the wellbore 100 can include oil, water, gas, other suitable material, or any suitable combination thereof.

At block 804, the asymmetric fluidic oscillator 400 oscillates the fluid from the wellbore 100. The inlet channel 402 of the asymmetric fluidic oscillator 400 can direct the fluid to the feedback system 404, which can oscillate the fluid. For example, the fluid can travel along the first feedback loop 410a, the second feedback loop 410b, within the mixing chamber 412, or any combination thereof. Accordingly, the fluid can vibrate, bounce, or otherwise oscillate within one or more components the asymmetric fluidic oscillator 400.

At block 806, the asymmetric fluidic oscillator 400 generates acoustic waves. The outlet channel 406 of the asymmetric fluidic oscillator 400 can receive the oscillated fluid from the feedback system 404, and the outlet channel 406 can interrupt the flow of the fluid via one or more asymmetric features of the outlet channel 406. For example, the asymmetric feature of the outlet channel 406 can interrupt (or otherwise disrupt) the flow of the fluid out of the asymmetric fluidic oscillator 400. The interruption or disruption of the flow of the fluid can cause pressure waves or other suitable acoustic signals to be generated using the asymmetric fluidic oscillator 400. The acoustic waves can propagate upstream from the asymmetric fluidic oscillator 400, downstream from the asymmetric fluidic oscillator 400, or a combination thereof. The acoustic signals can be detected in the wellbore 100 or in other locations such as proximate to a surface flow line of the wellbore 100, etc. For example, the acoustic waves can be detected using DAS system, for example via DAS measurements.

Sensors (e.g., the sensors 602a-b, the sensors 702a-b, DAS sensors, and the like) can be positioned with respect to the asymmetric fluidic oscillator 400 to detect the acoustic signals. For example, one or more sensors can be positioned upstream from the asymmetric fluidic oscillator 400, downstream with respect to the asymmetric fluidic oscillator, or a combination thereof. Additionally, the sensors can be positioned in (e.g., in the inlet channel 402, in the outlet channel 406, or in a combination thereof) the asymmetric fluidic oscillator 400, external and proximate with respect to the asymmetric fluidic oscillator, or a combination thereof. The sensors can be otherwise positioned with respect to the asymmetric fluidic oscillator 400 for detecting (or facilitating detection of) the acoustic waves generated via the asymmetric fluidic oscillator 400.

Figure 9:
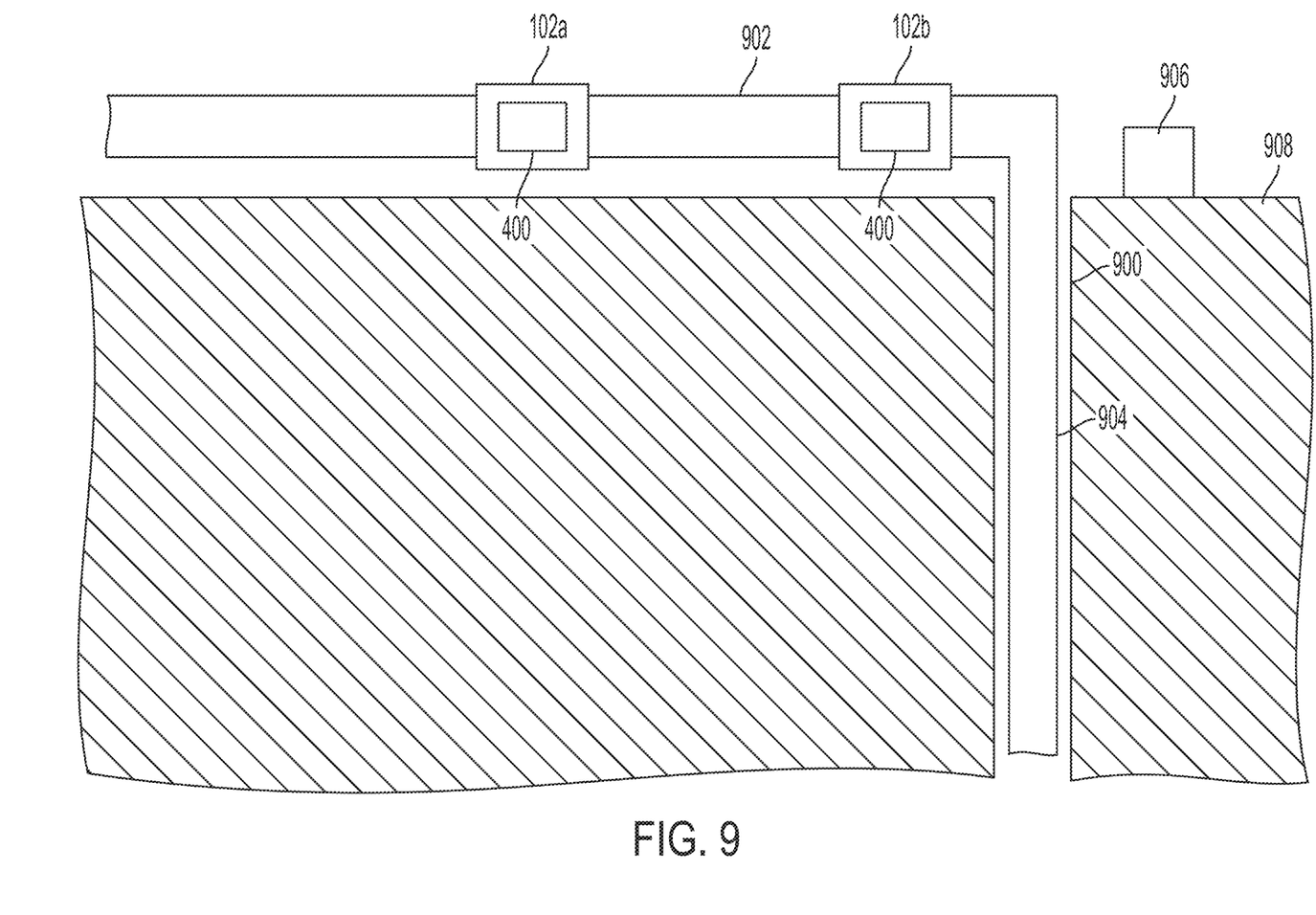
FIG. 9 is a diagram of a wellbore including a surface flow line that includes at least one flow meter device that includes an asymmetric fluidic oscillator according to one example of the present disclosure.

FIG. 9 is a diagram of a wellbore 900 including a surface flow line 902 that includes an asymmetric fluidic oscillator 400 according to one example of the present disclosure. As illustrated in FIG. 9, the surface flow line 902 includes two flow meter devices 102a-b, which can each include one or more asymmetric fluidic oscillators 400. The surface flow line 902 can include other suitable amounts of flow meter devices 102. The surface flow line 902 can include a number of flow meter devices 102 that corresponds to an amount of expected or actual phases in produced fluid from the wellbore 900. For example, if the produced fluid includes three phases (e.g., oil, water, and gas), then the surface flow line 902 may include three flow meter devices 102 for performing adequate multi-phase measurements of the produced fluid.

The surface flow line 902 can be coupled to a casing 904 or other suitable component of the wellbore 900 that can transport produced fluid from the wellbore 900. Additionally, the flow meter devices 102a-b of the surface flow line 902 may be communicatively coupled (e.g., via a wired connection, a wireless connection, or a combination thereof) to a detection system 906, which may be positioned at a surface 908 of the wellbore 900 or in other suitable locations such as in the wellbore 900, remote from the wellbore 900, and the like. The flow meter devices 102a-b can perform measurements (e.g., multi-phase measurements) relating to the produced fluid. For example, the flow meter devices 102a-b can measure (or facilitate measurement of) flow rate, fluid density, and the like with respect to the produced fluid, and the detection system 906 can receive (e.g., via the flow meter devices 102a-b, via detectors such as fiber-optic cables, etc.) the measurements for determining flow rate, fluid density, and the like with respect to the produced fluid from the wellbore 900.

In some aspects, fluidic oscillators, systems, and methods for generating acoustic signals detectable in a wellbore are provided according to one or more of the following examples.

As used below, any reference to a series of examples is to be understood as a reference to each of those examples disjunctively (e.g., "Examples 1-4" is to be understood as "Examples 1, 2, 3, or 4").

Example 1 is a fluidic oscillator comprising: an inlet housing defining an inlet channel sized to receive fluid from a wellbore; a feedback system coupled to the inlet channel to oscillate the fluid from the wellbore; and an outlet housing defining an outlet channel coupled to the feedback system and sized to receive the oscillated fluid from the feedback system, the outlet channel being asymmetric to generate acoustic signals detectable in the wellbore.

Example 2 is the fluidic oscillator of example 1, wherein the outlet channel includes an asymmetry along an axis oriented in a direction of flow of the fluid through the fluidic oscillator, and wherein flow of the fluid through the fluidic oscillator is interruptible using the outlet channel.

Example 3 is the fluidic oscillator of example 1, wherein the outlet housing comprises: a first lateral side coupled to a first side of the feedback system; a second lateral side positioned opposite the first lateral side; a bottom side coupled to a second side of the feedback system and to the second lateral side; and a top side coupled to the first lateral side and to the second lateral side, wherein the top side is open to direct the fluid out of the fluidic oscillator.

Example 4 is the fluidic oscillator of any of examples 1 and 3, wherein the first lateral side is longer than the second lateral side, wherein the bottom side is shorter than a distance between the first lateral side and the second lateral side, and wherein the bottom side is non-perpendicular to the second side of the feedback system and to the second lateral side.

Example 5 is the fluidic oscillator of example 1, wherein the outlet housing comprises: a first portion; and a second portion positioned opposite the first portion and separated by a buffer region, wherein the first portion comprises: a first lateral side; a second lateral side positioned opposite the first lateral side and coupled to a first side of the feedback system; a first bottom side coupled to the first lateral side and to the first side of the feedback system; and a first top side coupled to the first lateral side and to the second lateral side; and wherein the second portion comprises: a third lateral side coupled to a second side of the feedback system; a fourth lateral side positioned opposite the third lateral side; a second bottom side coupled to the fourth lateral side and to the second side of the feedback system; and a second top side coupled to the third lateral side and to the fourth lateral side.

Example 6 is the fluidic oscillator of any of examples 1 and 5, wherein the first top side is closed to interrupt flow of the fluid in the fluidic oscillator, and wherein the second top side is open to direct fluid out of the fluidic oscillator.

Example 7 is the fluidic oscillator of any of examples 1 and 5, wherein the outlet channel includes an asymmetry between the first portion and the second portion, wherein the asymmetry is along an axis in the buffer region, and wherein the axis is oriented in a direction of fluid flow through the fluidic oscillator.

Example 8 is a system comprising: a fluidic oscillator positionable in a wellbore, the fluidic oscillator comprising: an inlet housing defining an inlet channel sized to receive fluid from a wellbore; a feedback system coupled to the inlet channel to oscillate the fluid from the wellbore; and an outlet housing defining an outlet channel coupled to the feedback system and sized to receive the oscillated fluid from the feedback system, the outlet channel being asymmetric to generate acoustic signals detectable in the wellbore; and a measurement device positionable proximate to the fluidic oscillator to receive the acoustic signals.

Example 9 is the system of example 8, wherein the outlet channel includes an asymmetry along an axis oriented in a direction of flow of the fluid through the fluidic oscillator, and wherein flow of the fluid through the fluidic oscillator is interruptible using the outlet channel.

Example 10 is the system of example 8, wherein the outlet housing comprises: a first lateral side coupled to a first side of the feedback system; a second lateral side positioned opposite the first lateral side; a bottom side coupled to a second side of the feedback system and to the second lateral side; and a top side coupled to the first lateral side and to the second lateral side, wherein the top side is open to direct the fluid out of the fluidic oscillator.

Example 11 is the system of any of examples 8 and 10, wherein the first lateral side is longer than the second lateral side, wherein the bottom side is shorter than a distance between the first lateral side and the second lateral side, and wherein the bottom side is non-perpendicular to the second side of the feedback system and to the second lateral side.

Example 12 is the system of example 8, wherein the outlet housing comprises: a first portion; and a second portion positioned opposite the first portion and separated by a buffer region, wherein the first portion comprises: a first lateral side; a second lateral side positioned opposite the first lateral side and coupled to a first side of the feedback system; a first bottom side coupled to the first lateral side and to the first side of the feedback system; and a first top side coupled to the first lateral side and to the second lateral side; and wherein the second portion comprises: a third lateral side coupled to a second side of the feedback system; a fourth lateral side positioned opposite the third lateral side; a second bottom side coupled to the fourth lateral side and to the second side of the feedback system; and a second top side coupled to the third lateral side and to the fourth lateral side.

Example 13 is the system of any of examples 8 and 12, wherein the first top side is closed to interrupt flow of the fluid in the fluidic oscillator, and wherein the second top side is open to direct fluid out of the fluidic oscillator.

Example 14 is the system of any of examples 8 and 12, wherein the outlet channel includes an asymmetry between the first portion and the second portion, wherein the asymmetry is along an axis in the buffer region, and wherein the axis is oriented in a direction of fluid flow through the fluidic oscillator.

Example 15 is the system of example 8, further comprising a second measurement device, wherein the measurement device is positioned upstream with respect to the fluidic oscillator, wherein the second measurement device is positioned downstream with respect to the fluidic oscillator, and wherein the acoustic signals generated by the fluidic oscillator are detectable by the measurement device and by the second measurement device.

Example 16 is a method comprising: receiving fluid from a wellbore by an inlet channel of a fluidic oscillator; oscillating the fluid by a feedback system of the fluidic oscillator; outputting the fluid oscillated by the feedback system to an outlet channel that is asymmetric; and generating, by the outlet channel, a signal in the fluid from the feedback system.

Example 17 is the method of example 16, wherein the outlet channel includes an asymmetry along an axis oriented in a direction of flow of the fluid through the fluidic oscillator, and wherein generating the signal includes interrupting flow of the fluid through the fluidic oscillator using the outlet channel.

Example 18 is the method of example 16, wherein the outlet channel comprises: a first lateral side coupled to a first side of the feedback system; a second lateral side positioned opposite the first lateral side, wherein the first lateral side is longer than the second lateral side; a bottom side coupled to a second side of the feedback system and to the second lateral side, wherein the bottom side is shorter than a distance between the first lateral side and the second lateral side, wherein the bottom side is non-perpendicular to the second side of the feedback system and to the second lateral side; and a top side coupled to the first lateral side and to the second lateral side, wherein the top side is open to direct the fluid out of the fluidic oscillator.

Example 19 is the method of example 16, wherein the outlet channel comprises: a first portion; and a second portion positioned opposite the first portion and separated by a buffer region, wherein the outlet channel includes an asymmetry between the first portion and the second portion, wherein the asymmetry is along an axis in the buffer region, and wherein the axis is oriented in a direction of fluid flow through the fluidic oscillator, and wherein the first portion comprises: a first lateral side; a second lateral side positioned opposite the first lateral side and coupled to a first side of the feedback system; a first bottom side coupled to the first lateral side and to the first side of the feedback system; and a first top side coupled to the first lateral side and to the second lateral side; and wherein the second portion comprises: a third lateral side coupled to a second side of the feedback system; a fourth lateral side positioned opposite the third lateral side; a second bottom side coupled to the fourth lateral side and to the second side of the feedback system; and a second top side coupled to the third lateral side and to the fourth lateral side.

Example 20 is the method of any of examples 16 and 19, wherein generating the signal includes interrupting flow of the fluid in the fluidic oscillator by closing the first top side, further comprising directing the fluid out of the fluidic oscillator by opening the second top side.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A fluidic oscillator comprising:
   an inlet housing defining an inlet channel sized to receive fluid from a wellbore;
   a feedback system coupled to the inlet channel to oscillate the fluid from the wellbore; and
   an outlet housing defining an outlet channel coupled to the feedback system and sized to receive the oscillated fluid from the feedback system, the outlet channel being asymmetric to generate acoustic signals detectable in the wellbore, the outlet housing comprising:
   a pair of sides comprising a first side and a second side opposite one another and extending along a path of flow of the fluid, the first side coupled with the feedback system;
   a third side coupled to the feedback system and to the second side; and
   a fourth side extending from the first side to the second side, the fourth side open to direct the fluid out of the fluidic oscillator.

2. The fluidic oscillator of claim 1, wherein the outlet channel includes an asymmetry along an axis oriented in a direction of flow of the fluid through the fluidic oscillator, and wherein flow of the fluid through the fluidic oscillator is interruptible using the outlet channel.

3. The fluidic oscillator of claim 1, wherein
   the first side is coupled to a first lateral side of the feedback system; and
   the third side is coupled to a second lateral side of the feedback system.

4. The fluidic oscillator of claim 3, wherein the first side is longer than the second side, wherein the third side is shorter than a distance between the first side and the second side, and wherein the third side is non-perpendicular to the second side.

5. The fluidic oscillator of claim 1, wherein the outlet housing is a first outlet housing, wherein the fluidic oscillator further comprises a second outlet housing laterally offset from the first outlet housing, and wherein the second outlet housing comprises:
   a second pair of sides comprising a fifth side and a sixth side opposite one another and extending along a path of flow of the fluid, the fifth side coupled with the feedback system;
   a seventh side coupled to the feedback system and to the sixth side; and
   an eighth side extending from the fifth side to the sixth side, the eighth side open to direct the fluid out of the fluidic oscillator.

6. The fluidic oscillator of claim 5, wherein the fourth side is closed to interrupt flow of the fluid in the fluidic oscillator, and wherein the eighth side is open to direct fluid out of the fluidic oscillator.

7. The fluidic oscillator of claim 5, wherein the first outlet housing is asymmetric with respect to the second outlet housing, and wherein an asymmetry between the first outlet housing and the second outlet housing is along an axis in a buffer region between the first outlet housing and the second outlet housing, and wherein the axis is oriented in a direction of fluid flow through the fluidic oscillator.

8. A system comprising:
   a fluidic oscillator positionable in a wellbore, the fluidic oscillator comprising:
   an inlet housing defining an inlet channel sized to receive fluid from a wellbore;
   a feedback system coupled to the inlet channel to oscillate the fluid from the wellbore; and
   an outlet housing defining an outlet channel coupled to the feedback system and sized to receive the oscillated fluid from the feedback system, the outlet channel being asymmetric to generate acoustic signals detectable in the wellbore, the outlet housing comprising:
   a pair of sides comprising a first side and a second side opposite one another and extending along a path of flow of the fluid, the first side coupled with the feedback system;
   a third side coupled to the feedback system and to the second side; and
   a fourth side extending from the first side to the second side, the fourth side open to direct the fluid out of the fluidic oscillator; and a measurement device positionable proximate to the fluidic oscillator to receive the acoustic signals.

9. The system of claim 8, wherein the outlet channel includes an asymmetry along an axis oriented in a direction of flow of the fluid through the fluidic oscillator, and wherein flow of the fluid through the fluidic oscillator is interruptible using the outlet channel.

10. The system of claim 8, wherein
the first side is coupled to a first lateral side of the feedback system; and
the third side is coupled to a second lateral side of the feedback system.

11. The system of claim 10, wherein the first side is longer than the second side, wherein the third side is shorter than a distance between the first side and the second side, and wherein the third side is non-perpendicular to the second side of the feedback system and to the second side.

12. The system of claim 8, is a first outlet housing, wherein the fluidic oscillator further comprises a second outlet housing laterally offset from the first outlet housing, and wherein the second outlet housing comprises:
a second pair of sides comprising a fifth side and a sixth side opposite one another and extending along a path of flow of the fluid, the fifth side coupled with the feedback system;
a seventh side coupled to the feedback system and to the sixth side; and
an eighth side extending from the fifth side to the sixth side, the eighth side open to direct the fluid out of the fluidic oscillator.

13. The system of claim 12, wherein the fourth side is closed to interrupt flow of the fluid in the fluidic oscillator, and wherein the eighth side is open to direct fluid out of the fluidic oscillator.

14. The system of claim 12, wherein the first outlet housing is asymmetric with respect to the second outlet housing, and wherein an asymmetry between the first outlet housing and the second outlet housing is along an axis in a buffer region between the first outlet housing and the second outlet housing, and wherein the axis is oriented in a direction of fluid flow through the fluidic oscillator.

15. The system of claim 8, further comprising a second measurement device, wherein the measurement device is positioned upstream with respect to the fluidic oscillator, wherein the second measurement device is positioned downstream with respect to the fluidic oscillator, and wherein the acoustic signals generated by the fluidic oscillator are detectable by the measurement device and by the second measurement device.

16. A method comprising:
receiving fluid from a wellbore by an inlet channel of a fluidic oscillator;
oscillating the fluid by a feedback system of the fluidic oscillator;
outputting the fluid oscillated by the feedback system to an outlet channel that is asymmetric, the outlet channel comprising:
a pair of sides comprising a first side and a second side opposite one another and extending along a path of flow of the fluid, the first side coupled with the feedback system;
a third side coupled to the feedback system and to the second side; and
a fourth side extending from the first side to the second side, the fourth side open to direct the fluid out of the fluidic oscillator; and
generating, by the outlet channel, a signal in the fluid from the feedback system.

17. The method of claim 16, wherein the outlet channel includes an asymmetry along an axis oriented in a direction of flow of the fluid through the fluidic oscillator, and wherein generating the signal includes interrupting flow of the fluid through the fluidic oscillator using the outlet channel.

18. The method of claim 16, wherein:
the first side is coupled to a first lateral side of the feedback system,
wherein the first side is longer than the second side;
the third side is coupled to a second lateral side of the feedback system, wherein the third side is shorter than a distance between the first side and the second side, wherein the third side is non-perpendicular to the second side of the feedback system and to the second side.

19. The method of claim 16, wherein the outlet channel is a first outlet housing, wherein the fluidic oscillator further comprises a second outlet housing laterally offset from the first outlet housing, and wherein the second outlet housing comprises:
a second pair of sides comprising a fifth side and a sixth side opposite one another and extending along a path of flow of the fluid, the fifth side coupled with the feedback system;
a seventh side coupled to the feedback system and to the sixth side; and
an eighth side extending from the fifth side to the sixth side, the eighth side open to direct the fluid out of the fluidic oscillator.

20. The method of claim 19, wherein generating the signal includes interrupting flow of the fluid in the fluidic oscillator by closing the fourth side, further comprising directing the fluid out of the fluidic oscillator by opening the eighth side.

* * * * *